United States Patent [19]
Sakura et al.

[11] Patent Number: 5,615,009
[45] Date of Patent: Mar. 25, 1997

[54] METHOD OF STABILIZING SPECTRA IN SPECTROMETRY

[75] Inventors: Takeshi Sakura; Yutaka Yamasaki; Hiroko Kubo; Kexin Xu, all of Kyoto; Motonobu Shiomi, Neyagawa, all of Japan

[73] Assignees: Kyoto Daiichi Kagaku Co., Ltd., Kyoto; Kurashiki Boseki Kabushiki Kaisha, Okayama, both of Japan

[21] Appl. No.: 630,974

[22] Filed: Apr. 12, 1996

[30] Foreign Application Priority Data

Apr. 12, 1995 [JP] Japan ................................. 7-086795

[51] Int. Cl.$^6$ ............................................. G01J 3/42
[52] U.S. Cl. ............................................. 356/326
[58] Field of Search ................................. 356/326, 328

[56] References Cited

U.S. PATENT DOCUMENTS 4,715,712  12/1987  Nogami ................................. 356/328

Primary Examiner—F. L. Evans

[57] ABSTRACT

A method of quantitative analysis of a specific component of an object to be measured comprises steps of measuring an energy spectrum of light transmitted through or reflected from the object, dividing the energy spectrum into a plurality of wavelength domains, thereby obtaining a plurality of partial energy spectra, normalizing the plurality of partial energy spectra within each wavelength domain using an energy measured at a predetermined wavelength contained in each wavelength domain, and performing the quantitative analysis by multivariate analysis using the plurality of partial energy spectra having been normalized.

4 Claims, 18 Drawing Sheets

METHOD OF STABILIZING SPECTRA IN SPECTROMETRY

BACKGROUND OF THE INVENTION

1. Field of the Invention

The present invention relates to methods of stabilizing spectra in spectrometry and more particularly methods of stabilizing measurements by reducing in numerical computation the fluctuations of the spectral baseline due to changes in temperature, source voltage, and the like within the spectroscope and the fluctuations of transmittance due to changes in the incidence angle of the light applied to the measured object.

2. Description of the Related Art

In general, quantitative analysis for the concentration of a specified component can use an analytical curve obtained beforehand by measuring the energy spectrum of light transmitted through or alternatively reflected by a sample whose concentration is already known. As methods of obtaining the analytical curve, generally known are a method in which a single wavelength is used and a method in which two or more wavelengths are used.

However, fluctuations of the spectral baseline occur in the spectrum caused by changes in temperature inside and outside the spectroscope, changes in the voltage of the power supply, and the like. These fluctuations of the baseline reduce the accuracy of the quantitative analysis, so that it is necessary to eliminate the error components in the spectrum.

As methods of reducing the baseline fluctuations by numerical computation, double-wavelength baseline compensation, digital differentiation, and the low-frequency filtering Fourier transform are generally known. Each of these methods is briefly described in the following.

DOUBLE-WAVELENGTH BASELINE COMPENSATION.

The method of double-wavelength baseline compensation uses two wavelengths $\lambda_1$ and $\lambda_2$ at which the absorbances are constant for any solution composition to cancel the baseline component out. Specifically, the two wavelengths $\lambda_1$ and $\lambda_2$ respectively satisfy the following equations (1) and (2).

$$\sum_{i=1}^{n} \alpha_{i,\lambda_1} lc_i = const1 \text{(Constant)}, \qquad (1)$$

where $\alpha_{i,\lambda_1}$: absorptivity at wavelength $\lambda_1$, $c_i$: concentration of component i, n: the number of components in the solution, l: cell length.

$$\sum_{i=1}^{n} \alpha_{i,\lambda_2} lc_i = const2 \text{(Constant)}, \qquad (2)$$

where $\alpha_{i,\lambda_2}$: absorptivity at wavelength $\lambda_2$, $c_i$: concentration of component i, n: the number of components in the solution, l: cell length.

Therefore, if the absorbances of a measured absorption spectrum $f(\lambda)$ at wavelengths $\lambda_1$ and $\lambda_2$ are respectively const3 and const4, then the compensated spectrum is obtained by subtracting $(const4-const3)/(\lambda_2-\lambda_1) \times (\lambda-\lambda_1) + const3$ from $f(\lambda)$.

DIGITAL DIFFERENTIATION

The digital differentiation method reduces or eliminates a drift at a low frequency by digitally differentiating absorbance with respect to a wavelength. The order of differentiation is generally first or second. The constant component independent of wavelength can be eliminated by the first order differentiation. The first-order drift with respect to the wavelength can be eliminated by the second order differentiation. In digital differentiation, absorbance is differentiated with respect to the wavelength, so that differentiation higher than the second order greatly distorts the signal. Therefore, the digital differentiation of the order higher than third is rarely used.

LOW-FREQUENCY FILTERING FOURIER TRANSFORM

The method of the low-frequency filtering Fourier transform that Fourier transforms the spectrum, i.e., converts the energy spectrum from the time domain to the frequency domain, to filter out the low-frequency components that are the causes of the baseline shift.

The method of double-wavelength compensation requires the two wavelengths $\lambda_1$ and $\lambda_2$ used for compensation to respectively satisfy the above equations (1) and (2). However, in multi-component solutions of more than two components, there often do not exist the two wavelengths that satisfy the above equations (1) and (2). In these cases the method of double-wavelength compensation cannot be used.

The method of digital differentiation enlarges high-frequency noise such as random noise by digital differentiation. Therefore, the bandwidth of the baseline fluctuations has to be wider than the bandwidth of the light absorbed by substances. Further, the derivative spectra are distorted by digital differentiation.

In the method of the low-frequency filtering Fourier transform, there is a problem that the information about light absorption by substances in a low-frequency domain is lost by filtering together with baseline fluctuation components.

Further, there is a problem common to digital differentiation and the low-frequency filtering Fourier transform. That is, if the energy E is a function of two variables, time t and wavelength $\lambda$, then the total differential of $E(\lambda, t)$ is expressed by the following equation (3).

$$dE = (\partial E/\partial \lambda)_t d\lambda + (\partial E/\partial t)_\lambda dt. \qquad (3)$$

The prior methods of digital differentiation and the low-frequency filtering Fourier transform are both operations on wavelength $\lambda$. Therefore, the second term $(\partial E/\partial t)_\lambda$ of the equation (3), which is a function of t, can not be reduced or eliminated.

SUMMARY OF THE INVENTION

The object of the present invention is therefore to provide methods of stabilizing spectra in spectrometry such that spectral error components depending on time are reduced, and fluctuations of transmittance due to changes in the incidence angle of the light applied to the measured object are also reduced.

The present invention is based on the following consideration. Errors in an energy spectrum due to disturbances such as changes in temperature of the spectroscope, changes in the voltage of the power supply, and the like can generally be expressed as a drift, that is, a temporal change of the spectrum. Therefore, the intensity of transmitted light $I(\lambda, t)$ at wavelength $\lambda$ and time t and the intensity of the absorbed light at wavelength $\lambda_r$ and time t can be respectively expressed by the following equations (4) and (5).

$$I(\lambda,t) = k(\lambda,t) \cdot I_0(\lambda,t_0) \cdot p(\lambda,\theta) \cdot \exp\left[-\sum_i \alpha_i(\lambda)c_i l\right], \quad (4)$$

$$I(\lambda_r,t) = k(\lambda_r,t) \cdot I_0(\lambda_r,t_0) \cdot p(\lambda_r,\theta) \cdot \exp\left[-\sum_i \alpha_i(\lambda_r)c_i l\right]. \quad (5)$$

Here, $I(\lambda, t)$: intensity of transmitted light at wavelength $\lambda$ and time t, $I(\lambda_r, t)$: intensity of transmitted light at wavelength $\lambda_r$ and time t, $I_0(\lambda, t_0)$: intensity of incident light at wavelength $\lambda$ and time $t_0$, $I_0(\lambda_r, t_0)$: intensity of incident light at wavelength $\lambda_r$ and time $t_0$, $p(\lambda, \theta)$: surface transmittance of light incident at angle $\theta$ at wavelength $\lambda$, $p(\lambda_r, \theta)$: surface transmittance of light incident at angle $\theta$ at wavelength $\lambda_r$, $\alpha_i(\lambda)$: absorption coefficient of component i at wavelength $\lambda$, $\alpha_i(\lambda_r)$: absorption coefficient of component i at wavelength $\lambda_r$, $\theta$: incidence angle of light with the surface of the measured object $c_i$: concentration of component i, and $l$: effective path length.

Further, $k(\lambda, t)$ in the equation (4) is the ratio of the intensity of incident light at wavelength $\lambda$ and time t to the intensity $I_0(\lambda, t_0)$ of incident light at wavelength $\lambda$ and time $t_0$. Therefore, $$k(\lambda,t_0)=1. \quad (6)$$

Similarly, $k(\lambda_r, t)$ in the equation (5) is the ratio of the intensity of incident light at wavelength $\lambda_r$ and time t to the intensity $I_0(\lambda_r, t_0)$ of incident light at wavelength $\lambda_r$ and time $t_0$. Therefore, $$k(\lambda_r,t_0)=1. \quad (7)$$

The ratio of the equation (4) to the equation (5) yields the ratio $I_N$ of energy intensities expressed by the following equation (8).

$$I_N = \frac{k(\lambda,t)}{k(\lambda_r,t)} \cdot \frac{I_0(\lambda,t_0)}{I_0(\lambda_r,t_0)} \cdot \frac{p(\lambda,\theta)}{p(\lambda_r,\theta)} \quad (8)$$

$$\exp\left[-\sum_i (\alpha_i(\lambda)-\alpha_i(\lambda_r))c_i l\right].$$

Here, we assume $$\alpha_i(\lambda) \neq \alpha_i(\lambda_r). \quad (9)$$

The total differential of $k(\lambda, t)$ can be expressed by the following equation (10).

$$dk(\lambda,t)=(\partial k/\partial \lambda)_t d\lambda + (\partial k/\partial t)_\lambda dt. \quad (10)$$

Here, $(\partial k/\partial \lambda)_t$ expresses the dependency on wavelength of the ratio $k(\lambda, t)$ of intensities of incident light, and $(\partial k/\partial t)_\lambda$ expresses the rate of change with respect to time of the ratio $k(\lambda, t)$ of intensities of the incident light.

If the ratio of the intensity of incident light at time t and wavelength $\lambda$, i.e., $k(\lambda, t) \times I_0(\lambda, t)$, to the intensity of incident light at time t and wavelength $\lambda_r$, i.e., $k(\lambda, t) \times I_0(\lambda, t)$, is denoted by $\beta(\lambda, \lambda_r, t)$, then $$\beta(\lambda,\lambda_r,t) = \frac{k(\lambda,t)}{k(\lambda_r,t)} \cdot \frac{I_0(\lambda,t_0)}{I_0(\lambda_r,t_0)}. \quad (11)$$

Now, if the wavelength domain is divided into subintervals, and wavelengths $\lambda$ and $\lambda_r$ are limited to the jth subinterval $[\lambda_{j'min}, \lambda_{j'max}]$, then the term $(\partial k/\partial \lambda)_\lambda$, which expresses the dependency on wavelength of the ratio $k(\lambda, t)$, can be approximated by the following (12).

$$(\partial k/\partial \lambda)_t \approx 0. \quad (12)$$

Therefore, $$k(\lambda,t) \approx k(t). \quad (13)$$

Consequently, $\beta(\lambda, \lambda_r, t)$ can be expressed by the following equation (14), so that it can be also expressed as the equation (15).

$$\beta(\lambda,\lambda_r,t) = \frac{k(\lambda,t)}{k(\lambda_r,t)} \cdot \frac{I_0(\lambda,t_0)}{I_0(\lambda_r,t_0)} \quad (14)$$

$$= \frac{k(t)}{k(t)} \cdot \frac{I_0(\lambda,t_0)}{I_0(\lambda_r,t_0)}$$

$$= \frac{I_0(\lambda,t_0)}{I_0(\lambda_r,t_0)}.$$

$$\beta(\lambda,\lambda_r,t) \approx \beta(\lambda,\lambda_r). \quad (15)$$

From the above equation (15), it can be seen that error components due to the time dependent baseline drift mn in a spectrum can be reduced or eliminated.

Next, it is shown that the fluctuations of transmittance due to changes of the incidence angle of light can be reduced by obtaining the ratio of energy spectra in subdomains.

According to Fresnel's law, the surface transmittance $p(\lambda, \theta)$ when light is incident on the measured object at an incidence angle $\theta_i$ at wavelength $\lambda$ and the surface transmittance $p(\lambda_r, \theta)$ when light is incident on the measured object at an incidence angle $\theta_i$ at wavelength $\lambda_r$ can respectively be expressed by the following equations (16), (17), (18), and (19).

$$p(\lambda,\theta)_\| = \frac{n_{2,\lambda}}{n_{1,\lambda}} \cdot \frac{\cos\theta_t}{\cos\theta_i} \cdot \left(\frac{2n_{1,\lambda}\cos\theta_i}{n_{2,\lambda}\cos\theta_i + n_{1,\lambda}\cos\theta_t}\right)^2. \quad (16)$$

$$p(\lambda,\theta)_\perp = \frac{n_{2,\lambda}}{n_{1,\lambda}} \cdot \frac{\cos\theta_t}{\cos\theta_i} \cdot \left(\frac{2n_{1,\lambda}\cos\theta_i}{n_{1,\lambda}\cos\theta_i + n_{2,\lambda}\cos\theta_t}\right)^2. \quad (17)$$

$$p(\lambda_r,\theta)_\| = \frac{n_{2,\lambda}}{n_{1,\lambda}} \cdot \frac{\cos\theta_t}{\cos\theta_i} \cdot \left(\frac{2n_{1,\lambda_r}\cos\theta_i}{n_{2,\lambda_r}\cos\theta_i + n_{1,\lambda_r}\cos\theta_t}\right)^2. \quad (18)$$

$$p(\lambda_r,\theta)_\perp = \frac{n_{2,\lambda}}{n_{1,\lambda}} \cdot \frac{\cos\theta_t}{\cos\theta_i} \cdot \left(\frac{2n_{1,\lambda_r}\cos\theta_i}{n_{1,\lambda_r}\cos\theta_i + n_{2,\lambda_r}\cos\theta_t}\right)^2. \quad (19)$$

Here, $p(\lambda,\theta_i)_\|$: surface transmittance of light at wavelength $\lambda$ when horizontally polarized light is incident on the measured object at the incidence angle $\theta_i$, $p(\lambda, \theta)_\perp$: surface transmittance of light at wavelength $\lambda$ when vertically polarized light is incident on the measured object at the incidence angle $\theta_i$, $p(\lambda_r, \theta)_\|$: surface transmittance of light at wavelength $\lambda_r$ when horizontally polarized light is incident on the measured object at the incidence angle $\theta_i$, $p(\lambda_r, \theta)_\perp$: surface transmittance of light at wavelength $\lambda_r$ when vertically polarized light is incident on the measured object at the incidence angle $\theta_i$, $n_{1,\lambda}$: index of refraction of medium 1 at wavelength $\lambda$, $n_{2,\lambda}$: index of refraction of medium 2 at wavelength $\lambda$, $n_{1,\lambda_r}$: index of refraction of medium 1 at wavelength $\lambda_r$, $n_{2,\lambda_r}$: index of refraction of medium 2 at wavelength $\lambda_r$:

$\theta_i$: incidence angle with the surface of measured object, and $\theta_t$: refraction angle with the surface of measured object.

Further, according to Snell's law, the following equation (20) holds.

$$n_1 \sin \theta_i = n_2 \sin \theta_t. \quad (20)$$

Now, the ratio of $p(\lambda, \theta)$ to $p(\lambda_r, \theta)$ is denoted by $\gamma(\lambda, \lambda_r, \theta)$, i.e., $$\gamma(\lambda, \lambda_r, \theta) = p(\lambda, \theta)/p(\lambda_r, \theta). \quad (21)$$

If $\Delta\lambda = \lambda_r - \lambda$ is small, then $\gamma(\lambda, \lambda_r, \theta)$ can be approximated by $$\gamma(\lambda, \lambda_r, \theta) \approx \gamma(\lambda, \lambda_r). \quad (22)$$

From the equations (8), (15), and (22), we obtain the following equation (23).

$$I_N \approx \beta(\lambda, \lambda_r) \cdot \gamma(\lambda, \lambda_r) \cdot \exp\left[ -\sum_i (\alpha_i(\lambda) - \alpha_i(\lambda_r)) c_i l \right].$$

It is seen from the above equation (23) that errors of baseline fluctuations of the spectrum due to time dependence and fluctuations of transmittance due to changes of the incidence angle of the incident light can be reduced at the same time.

The present invention is based on the consideration described above. The method of the present invention is a method of spectrometry that performs quantitative analysis of a specific component of a measured object by irradiating the measured object with light and measuring the energy spectrum of the transmitted light or alternatively the energy spectrum of the reflected light. In particular, the method divides the wavelength domain of the measured energy spectrum of the transmitted light or the reflected light into a plurality of intervals. Then the method obtains, within each interval, the ratio of each measured energy value to the measured energy value at a predetermined wavelength to stabilize the measured values of the spectrum. In this way, the quantitative analysis of the specific component can be achieved with stabilized spectral values.

Further, according to one embodiment of the present invention, there is provided a method of stabilizing spectra in spectrometry that performs quantitative analysis of a specific component of a measured object by irradiating the measured object with light and measuring the energy spectrum of the transmitted light or alternatively the energy spectrum of the reflected light. In particular, the method divides the wavelength domain of the measured energy spectrum of the transmitted light or the reflected light into a plurality of intervals. Then the method obtains, within each interval, the ratio of each measured energy value to the measured energy value at a predetermined wavelength to stabilize the measured values of the spectrum. Then the method performs multivariate analysis for the spectrum of the ratios. In this way, the quantitative analysis of the specific component can be achieved with stabilized spectral values.

Further, in the present invention, the specific component of the measured object is glucose.

A method of the present invention divides the wavelength domain of the measured energy spectrum of the transmitted light or the reflected light into a plurality of intervals. Then the method obtains, within each interval, the ratio of each measured energy value to the measured energy value at a predetermined wavelength to stabilize the measured values of the spectrum. In this way, errors of baseline fluctuations of the spectrum due to time dependence and fluctuations of transmittance due to the incidence angle of the incident light can be compensated at the same time.

Further, a method of present invention performs multivariate analysis for the spectrum obtained by the ratios of energy spectra in subdomains.

In particular, the energy spectrum of transmitted light or the energy spectrum of reflected light for glucose is compensated by taking ratios in subdomains.

According to the present invention, errors of baseline fluctuations of the spectrum due to time dependence and fluctuations of transmittance due to the incidence angle of the incident light can be reduced at the same time. Consequently, the accuracy and reliance of quantitative analysis in spectrometry can be improved.

Further, according to the present invention, the accuracy and reliance of quantitative analysis can be improved by multivariate analysis.

Still further, according to the present invention, in the case of glucose being the specific component, the concentration of glucose can be detected with great accuracy by applying the methods of the present invention, so that the measurement of blood sugar in human body can be obtained with great accuracy and reliance.

BRIEF DESCRIPTION OF THE DRAWINGS

These and other objects and features of the present invention will become clear from the following description taken in conjunction with the embodiments thereof with reference to the accompanying drawings, in which.

DETAILED DESCRIPTION OF THE PREFERRED EMBODIMENTS

The preferred embodiments according to the present invention will be described below with reference to the attached drawings.

FIRST EMBODIMENT

We filled a quartz cell with commercial milk. Then, using an infrared spectroscope manufactured by Parkin-Elmer Co., we measured the energy spectra of transmitted light 11 times every 5 minutes on the domain of wavelengths from 4000 $cm^{-1}$ to 8000 $cm^{-1}$. Then we performed, for the measurements of the transmitted energy spectrum, (1) no processing, (2) processing of obtaining the ratio of each measured energy value to the measured energy value at a single wavelength, (3) processing of obtaining the ratio of each measured energy value to the measured energy value at a predetermined wavelength within each subdomain, (4) first-order differentiation, (5) second-order differentiation, and (6) the Fourier transform. Further, we calculated the CV values (=100× standard deviation/mean) of the energy spectrum of transmitted light at each selected wavelength in the wavelength domain of 4000 $cm^{-1}$ to 8000 $cm^{-1}$. The spectrum obtained by plotting CV values at every selected wavelength is called a CV spectrum in the following.

Figure 1:
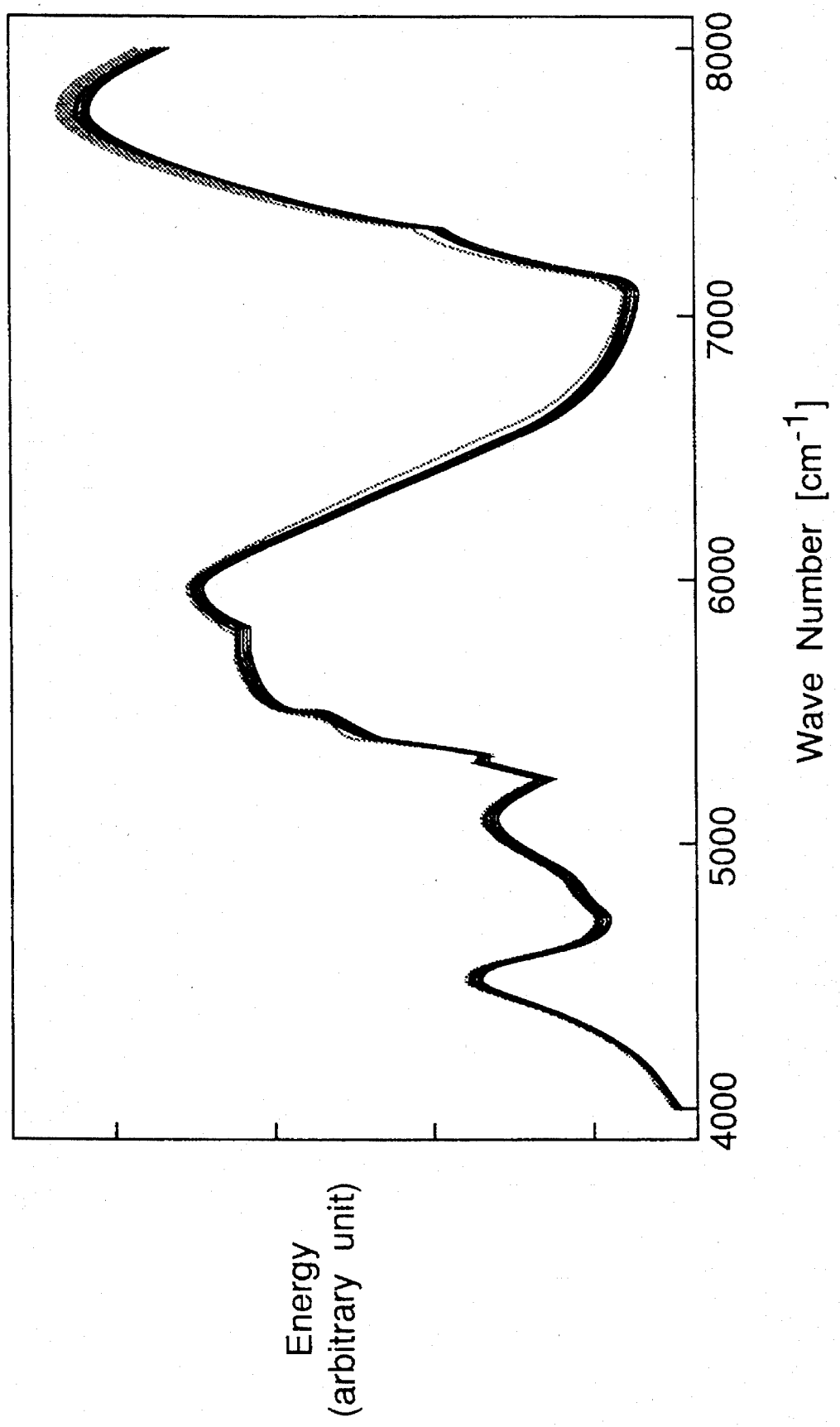
FIG. 1 shows 11 energy spectra of transmitted light of commercial milk measured every 5 minutes.
Figure 2:
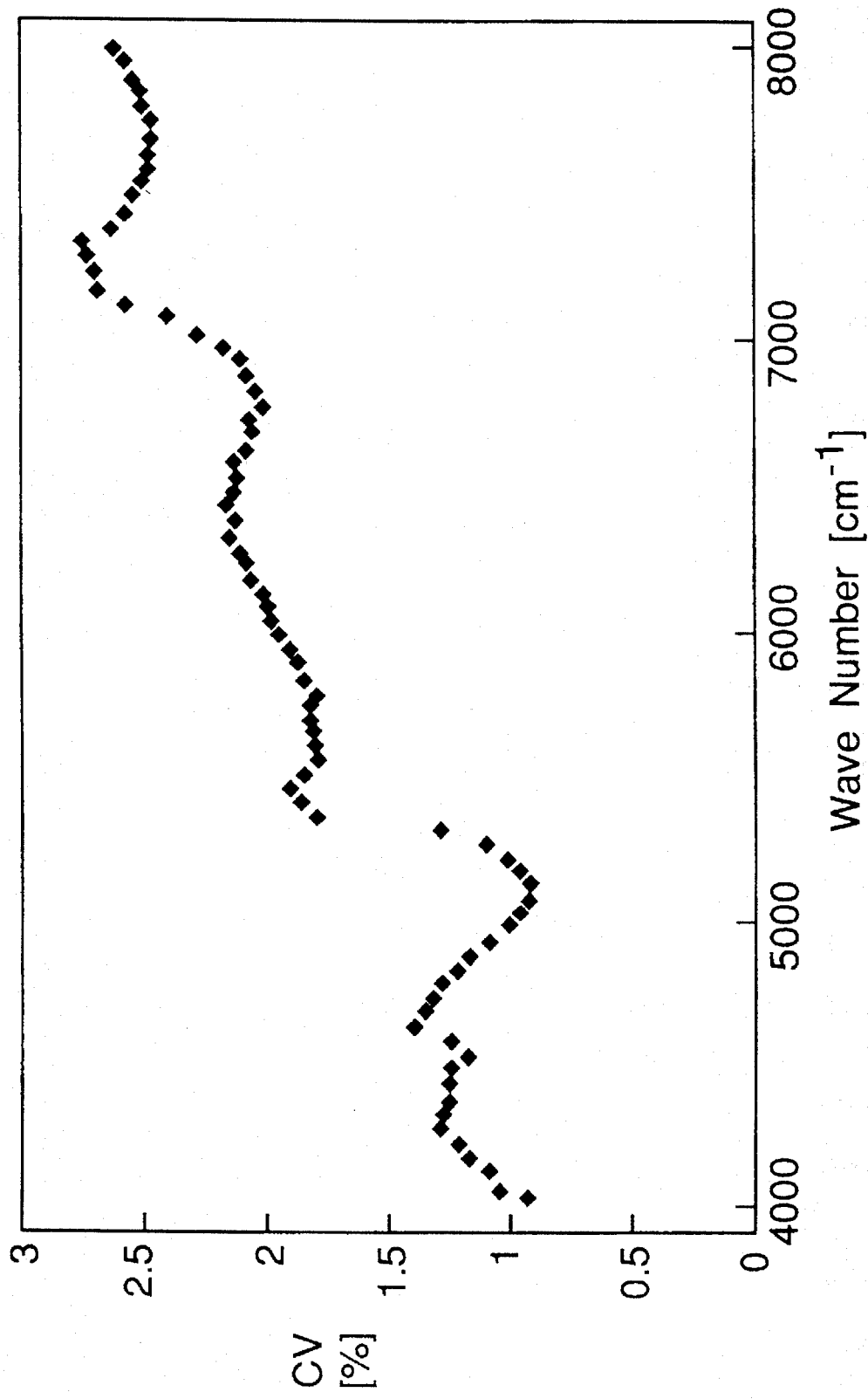
FIG. 2 shows the CV spectrum of the spectra shown in FIG. 1.

(1) No processing:

The 11 energy spectra of transmitted light measured every 5 minutes of the commercial milk are shown in FIG. 1. Their CV spectrum is shown in FIG. 2.

Figure 3:
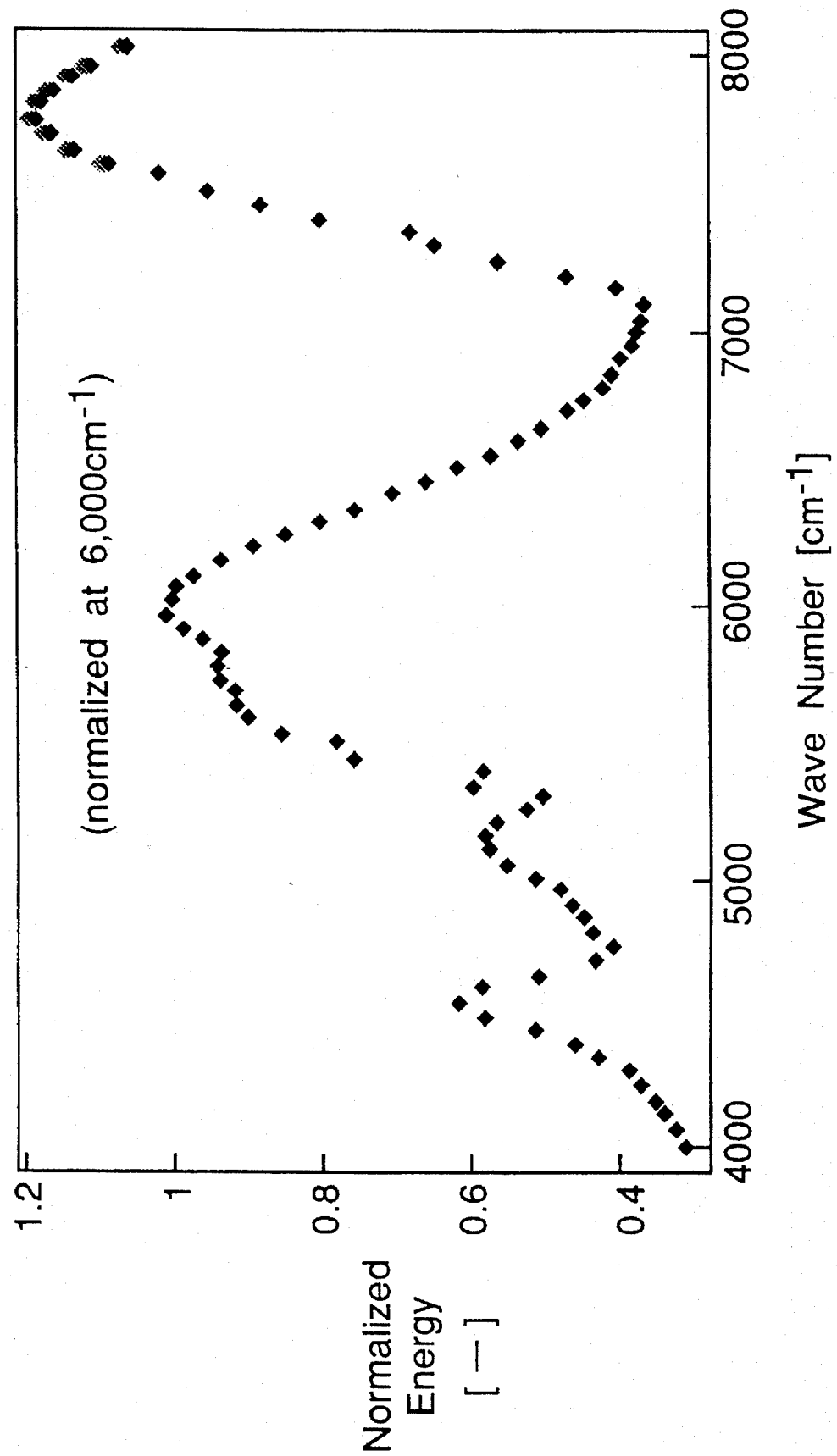
FIG. 3 shows energy spectra obtained by taking the ratios of each measured energy value to the measured energy value at wavelength 6000 cm$^{-1}$.
Figure 4:
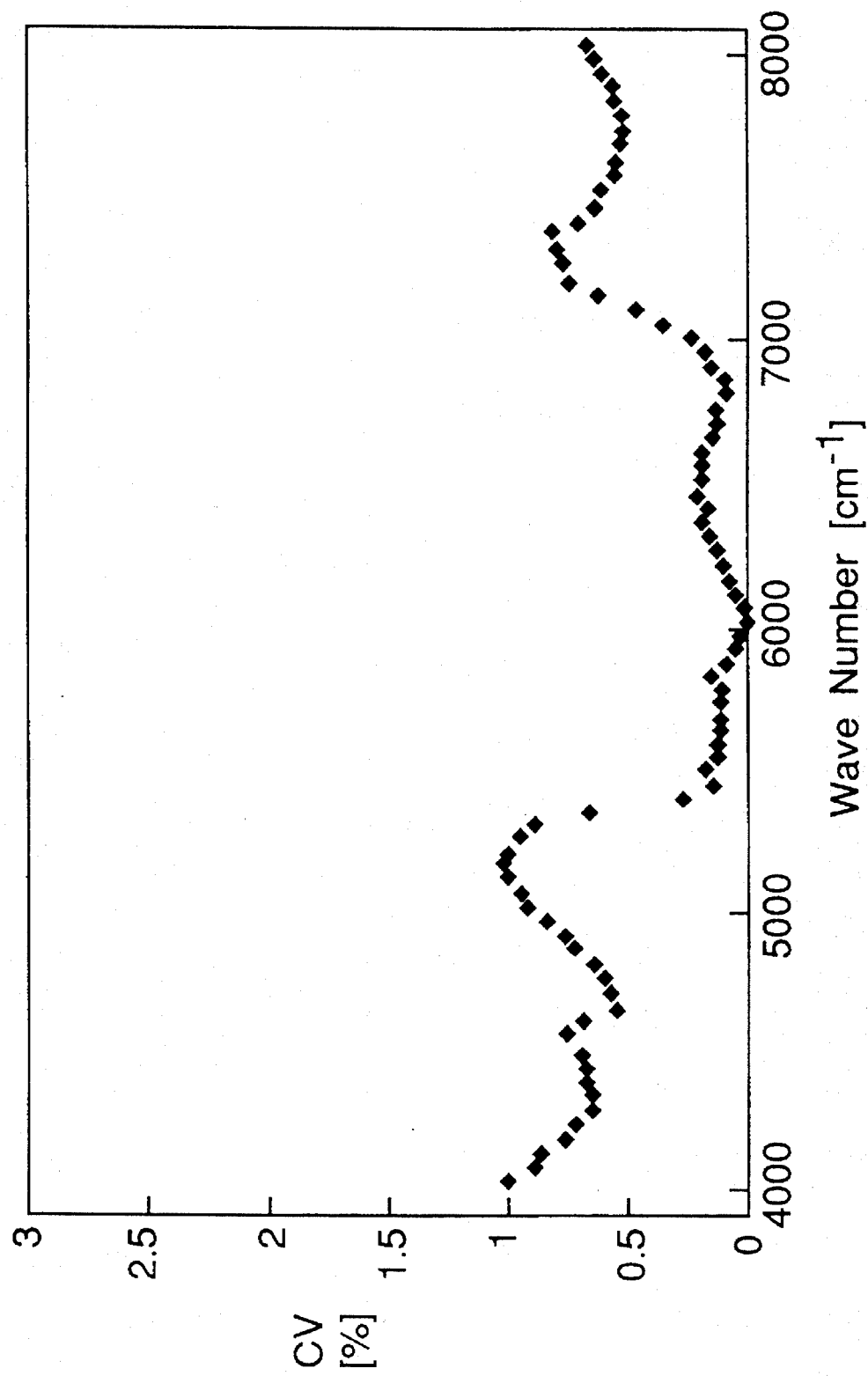
FIG. 4 shows the CV spectrum of the spectra shown in FIG. 3.

(2) Ratio calculation for single wavelength:

The ratio spectra of the 11 energy spectra of transmitted light shown in FIG. 1 obtained by calculating the ratio of each measured energy value to the measured energy value at wavelength 6000 $cm^{-1}$ are shown in FIG. 3. Their CV spectrum is shown in FIG. 4.

Figure 5:
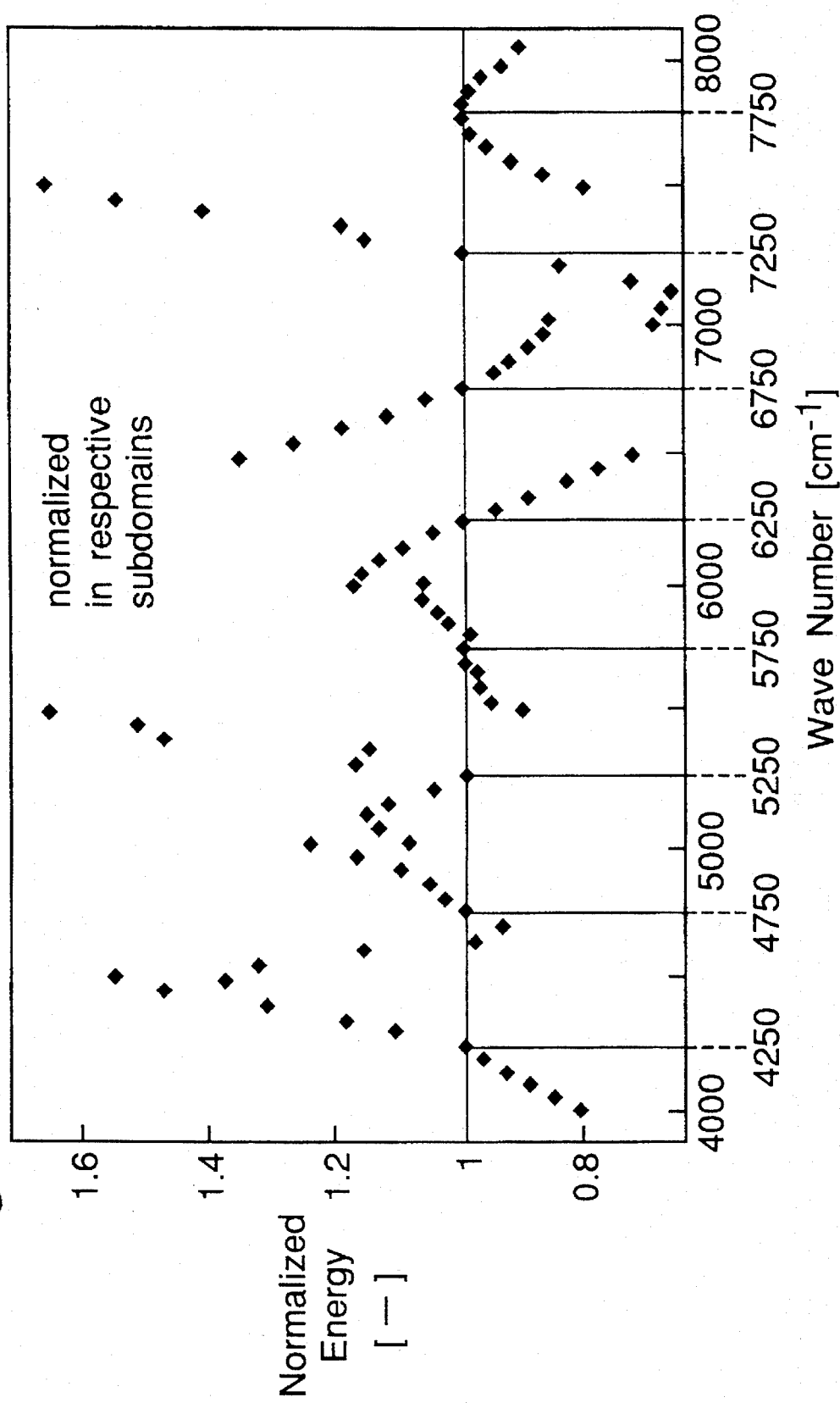
FIG. 5 shows energy spectra obtained by taking ratios in subdomains.
Figure 6:
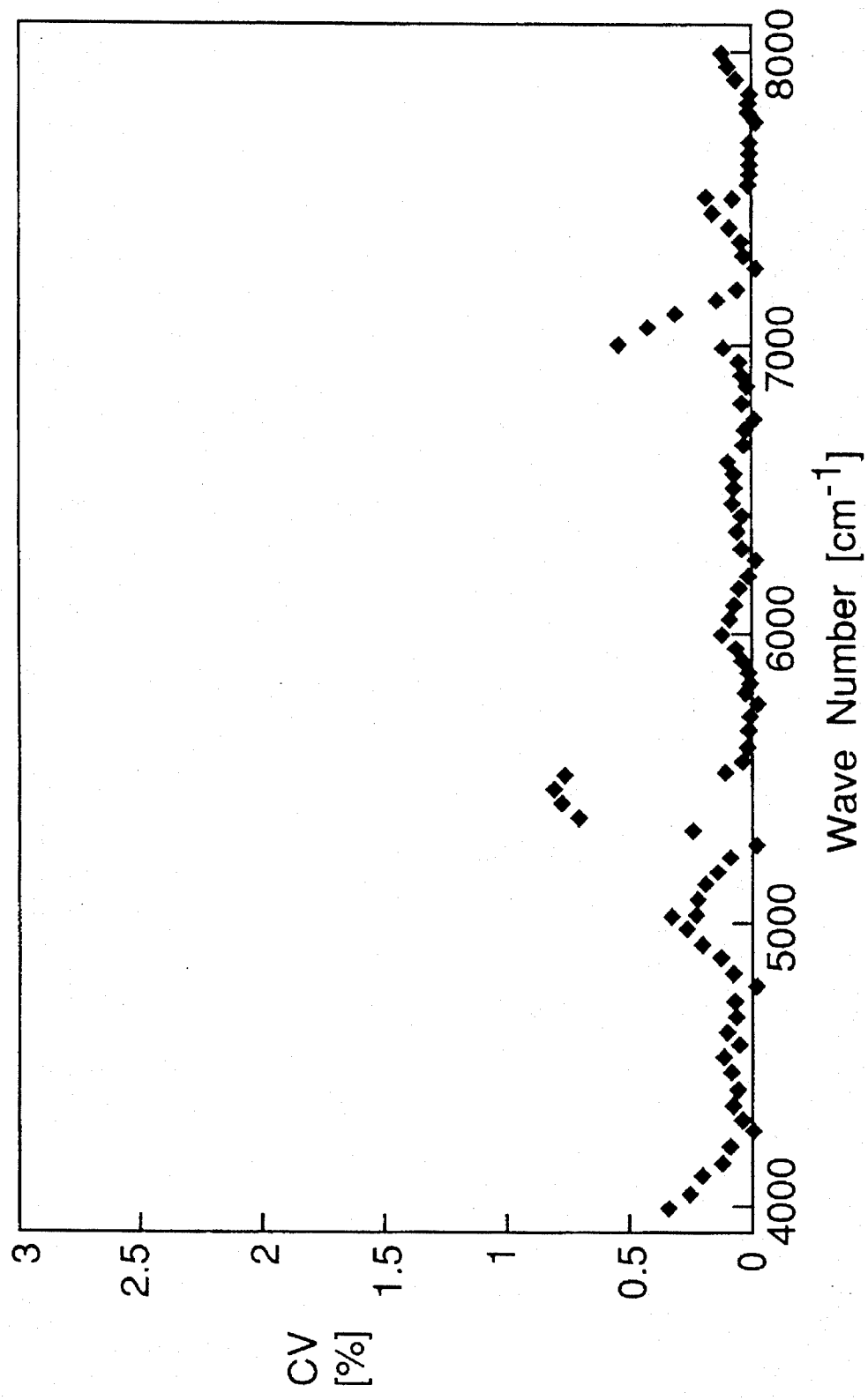
FIG. 6 shows the CV spectrum of the spectra shown in FIG. 5.
Figure 7:
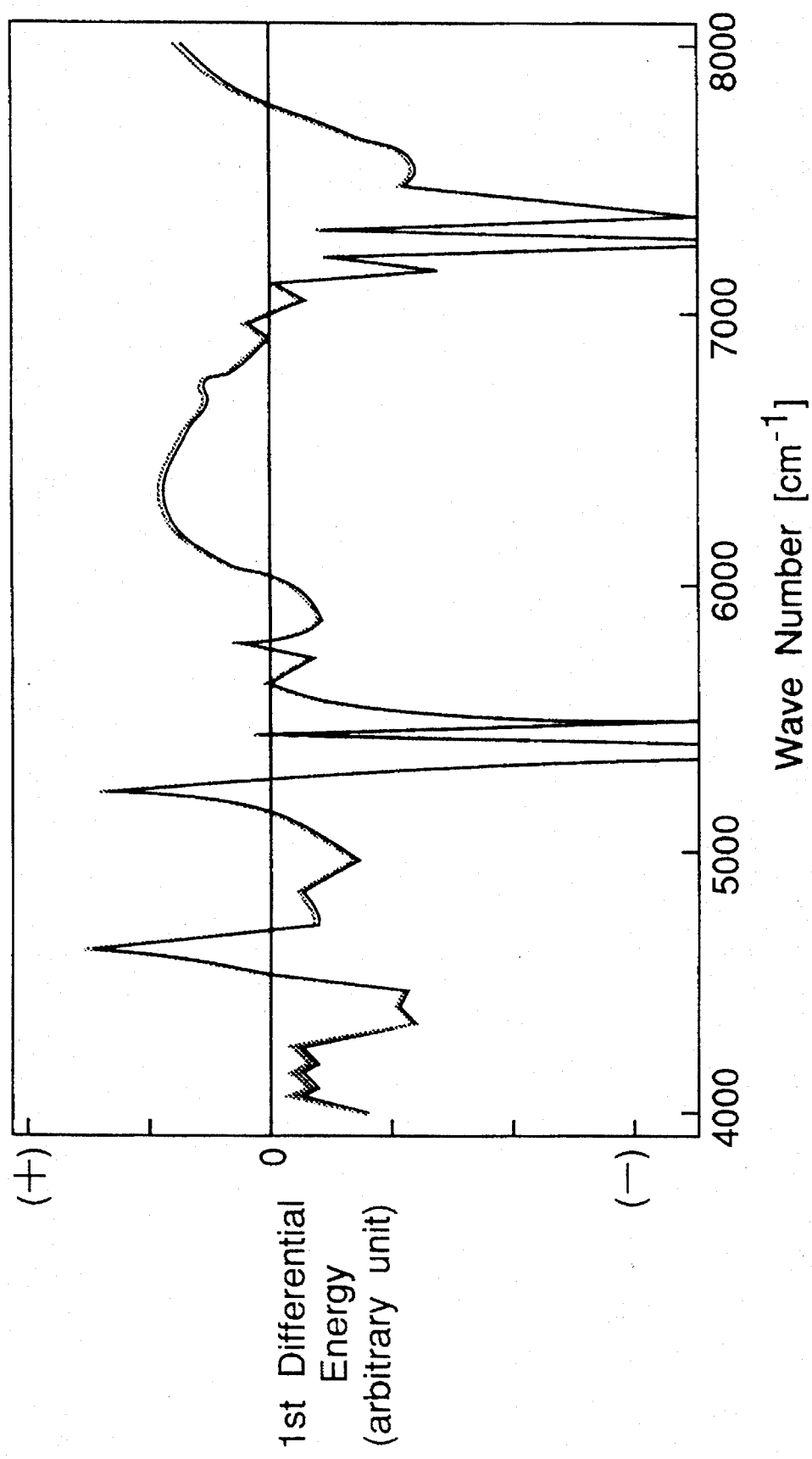
FIG. 7 shows energy spectra obtained by first-order differentiation of the energy spectra shown in FIG. 1.

(3) Ratio calculation in subdomains:

We divided the wavelength domain of 4000 $cm^{-1}$ to 8000 $cm^{-1}$ of the energy spectrum of transmitted light of the 11 commercial milk measured every 5 minutes into the following 8 wavelength subdomains:

4000 $cm^{-1}$ to 4500 $cm^{-1}$ (4250 $cm^{-1}$),
4500 $cm^{-1}$ to 5000 $cm^{-1}$ (4750 $cm^{-1}$),
5000 $cm^{-1}$ to 5500 $cm^{-1}$ (5250 $cm^{-1}$),
5500 $cm^{-1}$ to 6000 $cm^{-1}$ (5750 $cm^{-1}$),
6000 $cm^{-1}$ to 6500 $cm^{-1}$ (6250 $cm^{-1}$),
6500 $cm^{-1}$ to 7000 $cm^{-1}$ (6750 $cm^{-1}$),
7000 $cm^{-1}$ to 7500 $cm^{-1}$ (7250 $cm^{-1}$),
7500 $cm^{-1}$ to 8000 $cm^{-1}$ (7750 $cm^{-1}$),

Then, we divided each energy spectrum of transmitted light belonging to each subdomain by the energy value at the wavelength shown within the parentheses to obtain the ratio spectra on the whole domain as shown in FIG. 5. Their CV spectrum is shown in FIG. 6.

Figure 8:
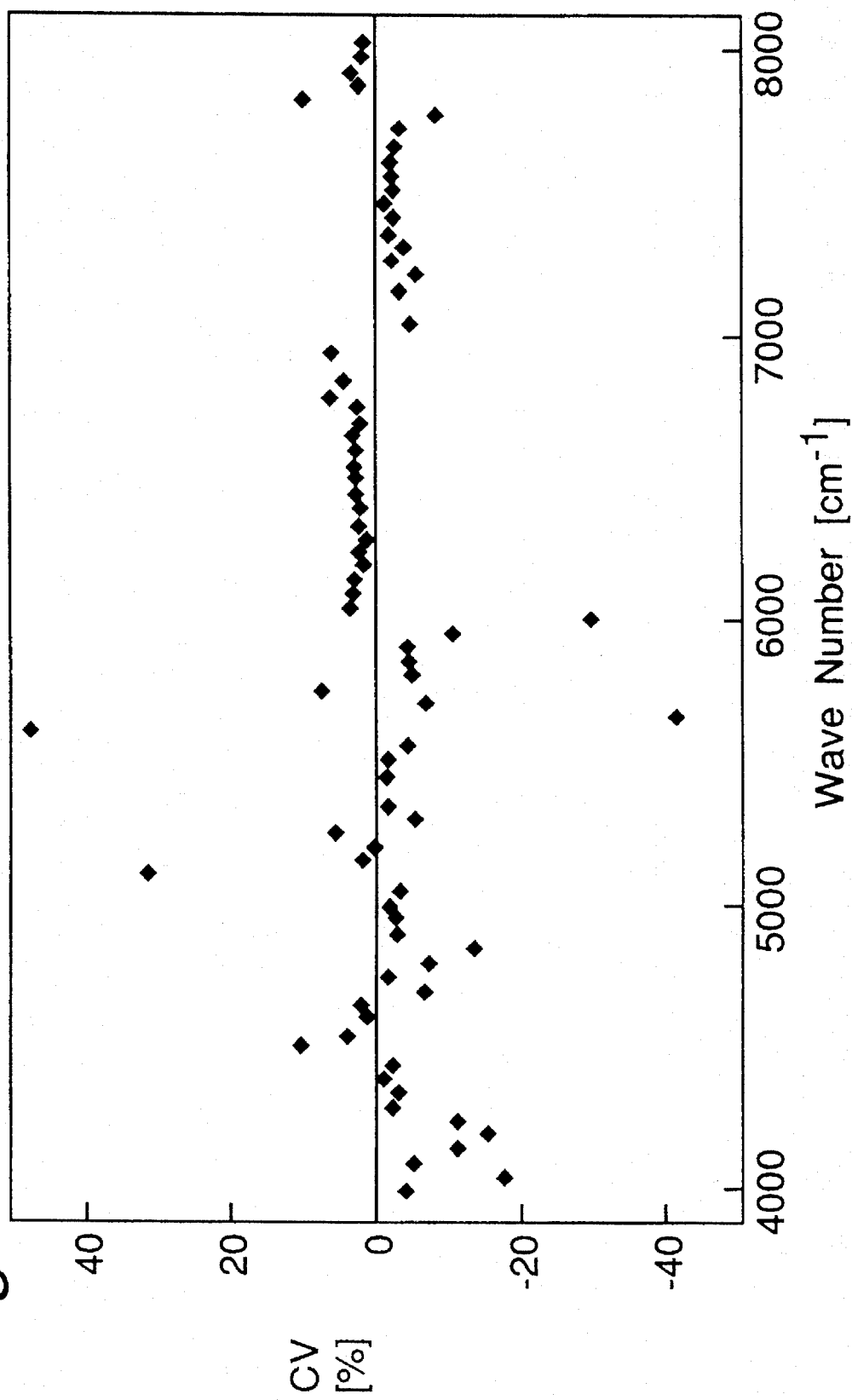
FIG. 8 shows the CV spectrum of the spectra shown in FIG. 7.

(4) First-order differentiation:

The first-order differential spectra obtained from the 11 energy spectra of transmitted light measured every 5 minutes of the commercial milk shown in FIG. 1 are shown in FIG. 8. Their CV spectrum is shown in FIG. 8.

Figure 9:
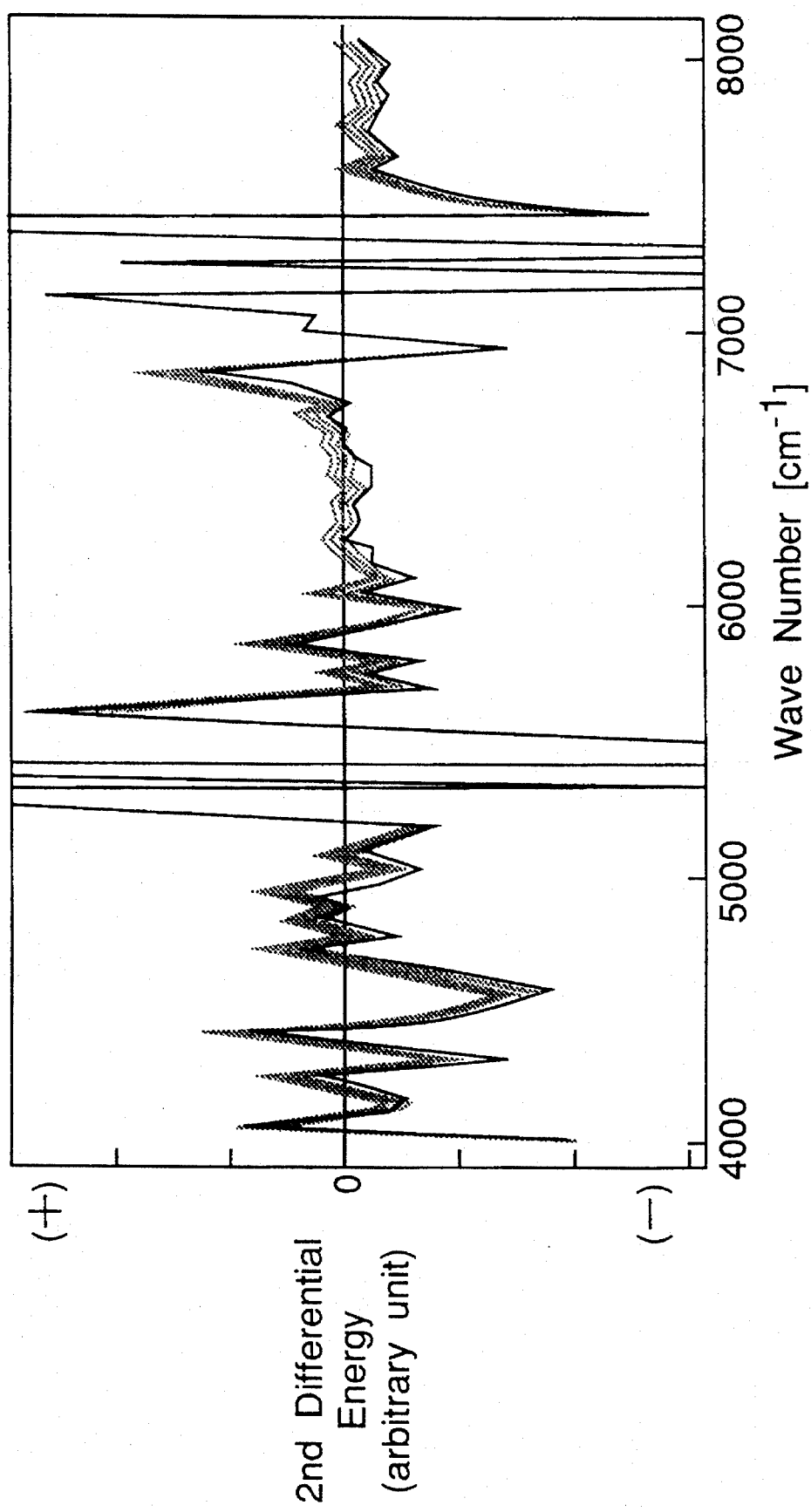
FIG. 9 shows spectra obtained by second-order differentiation of the energy spectra shown in FIG. 1.
Figure 10:
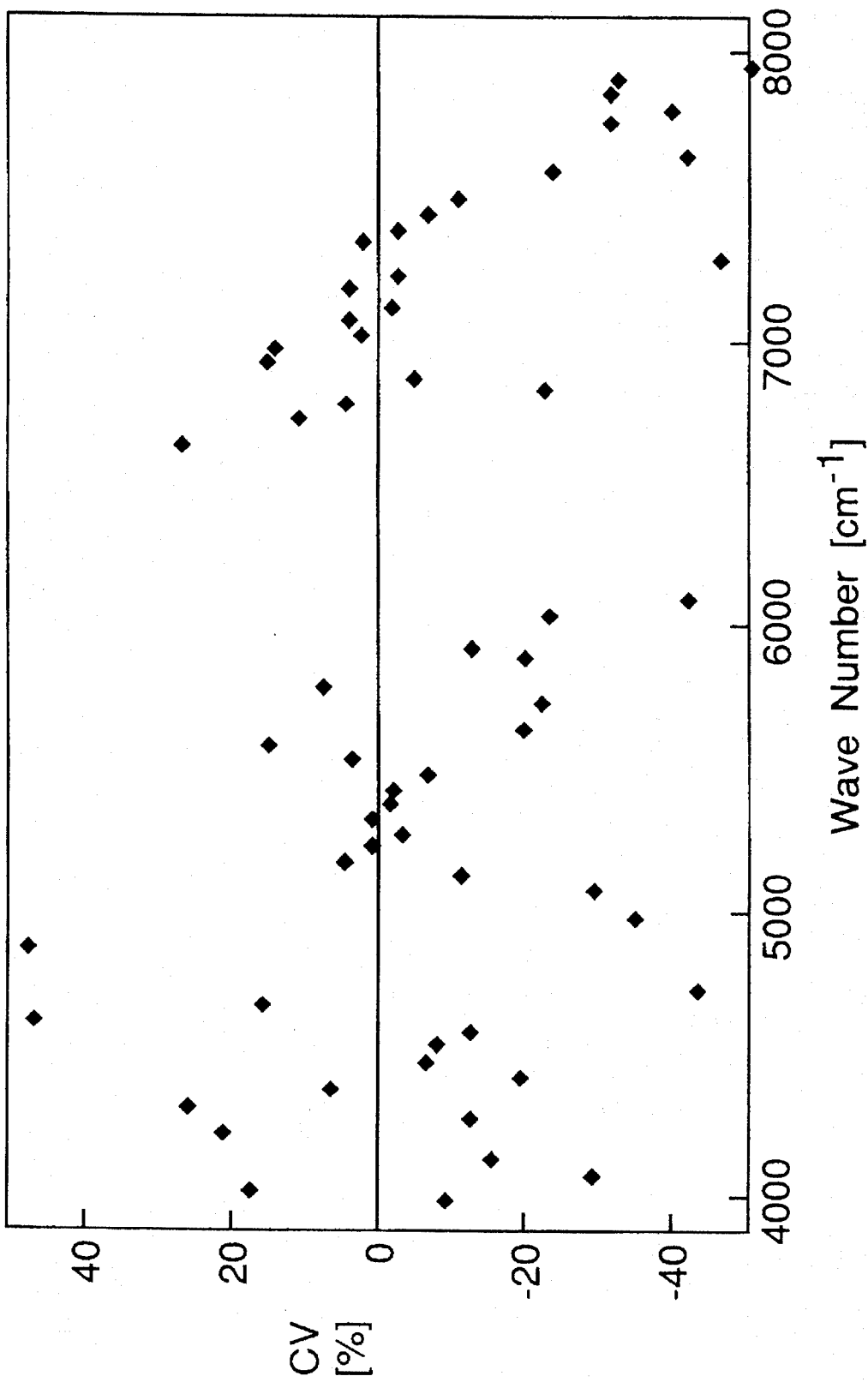
FIG. 10 shows the CV spectrum of the spectra shown in FIG. 9.

(5) Second-order differentiation:

The second-order differential spectra obtained from the 11 energy spectra of transmitted light measured every 5 minutes of the commercial milk shown in FIG. 1 are shown in FIG. 9. Their CV spectrum is shown in FIG. 10.

Figure 11:
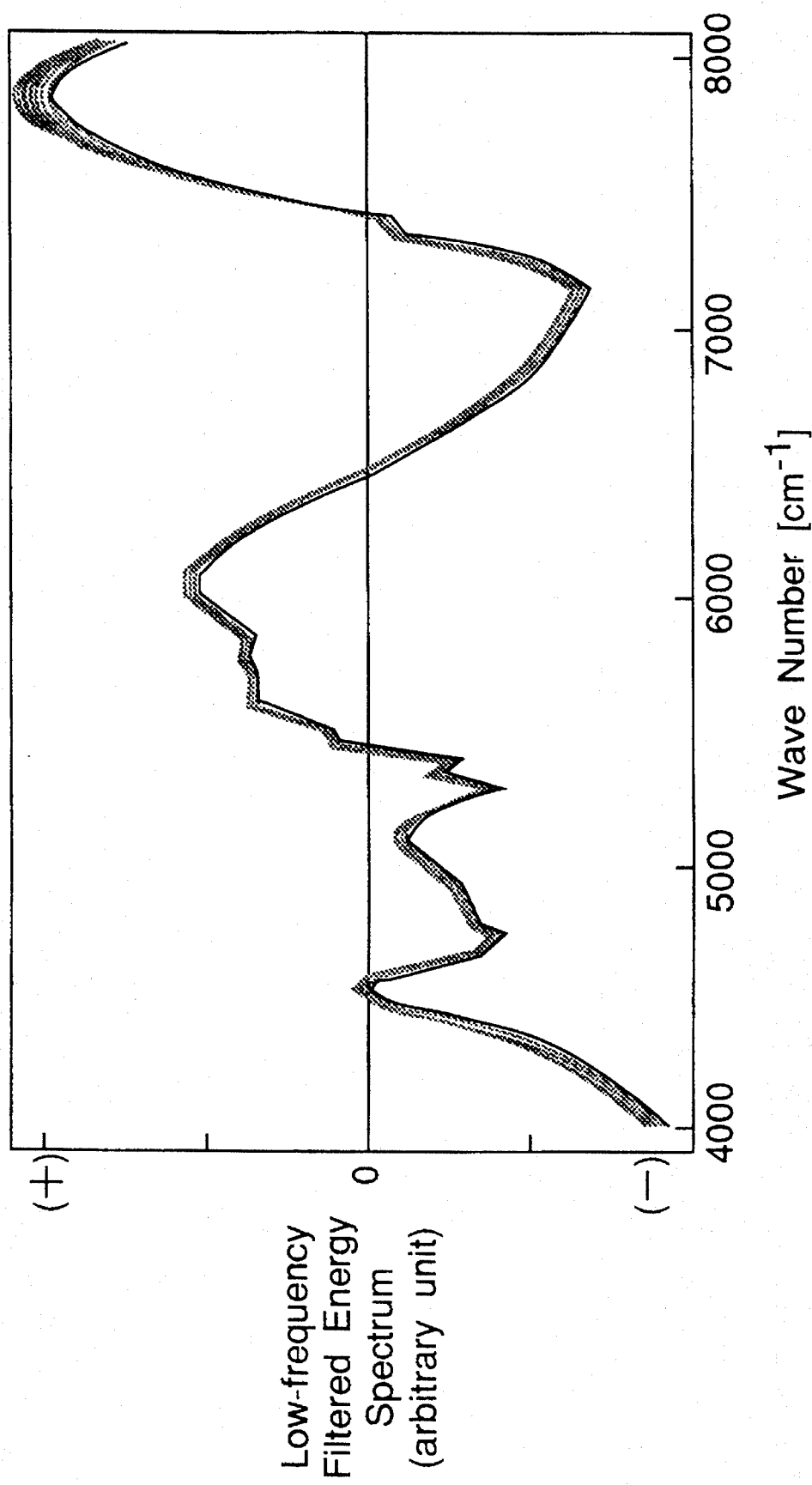
FIG. 11 shows energy spectra obtained by the low-frequency filtering Fourier transform.
Figure 12:
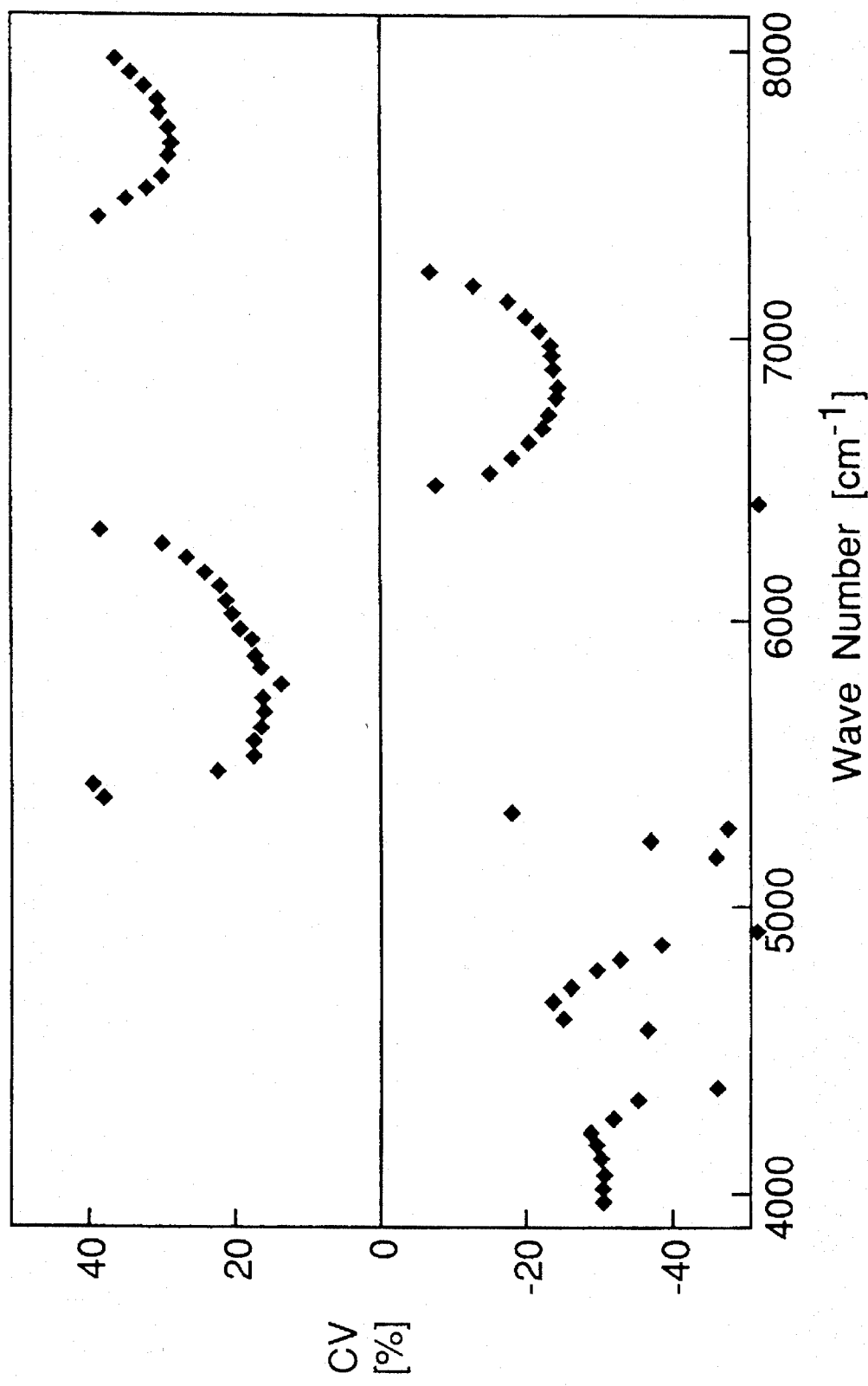
FIG. 12 shows the CV spectrum of the spectra shown in FIG. 11.
Figure 13:
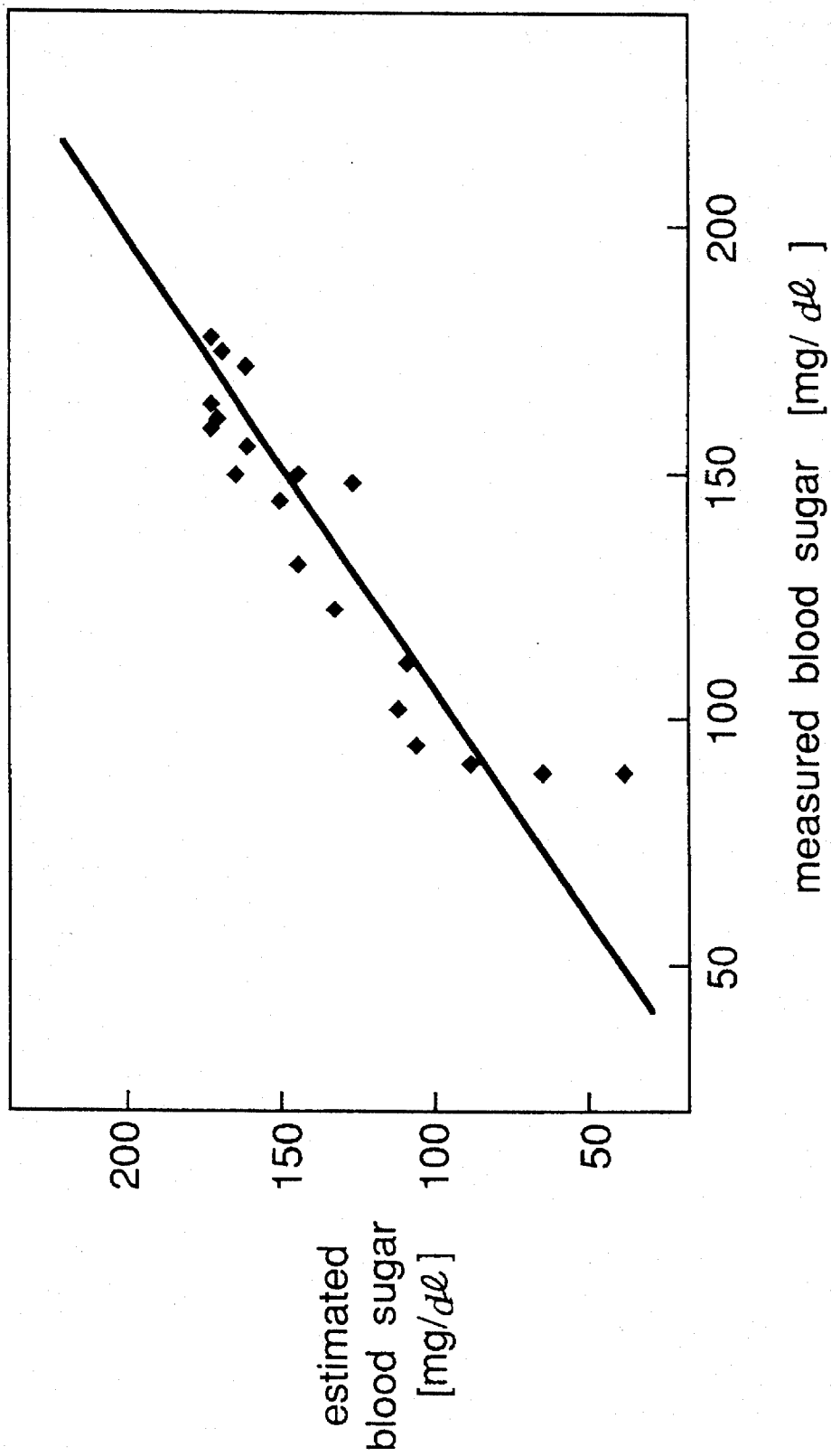
FIG. 13 shows results of quantitative analysis in the case of no processing.
Figure 14:
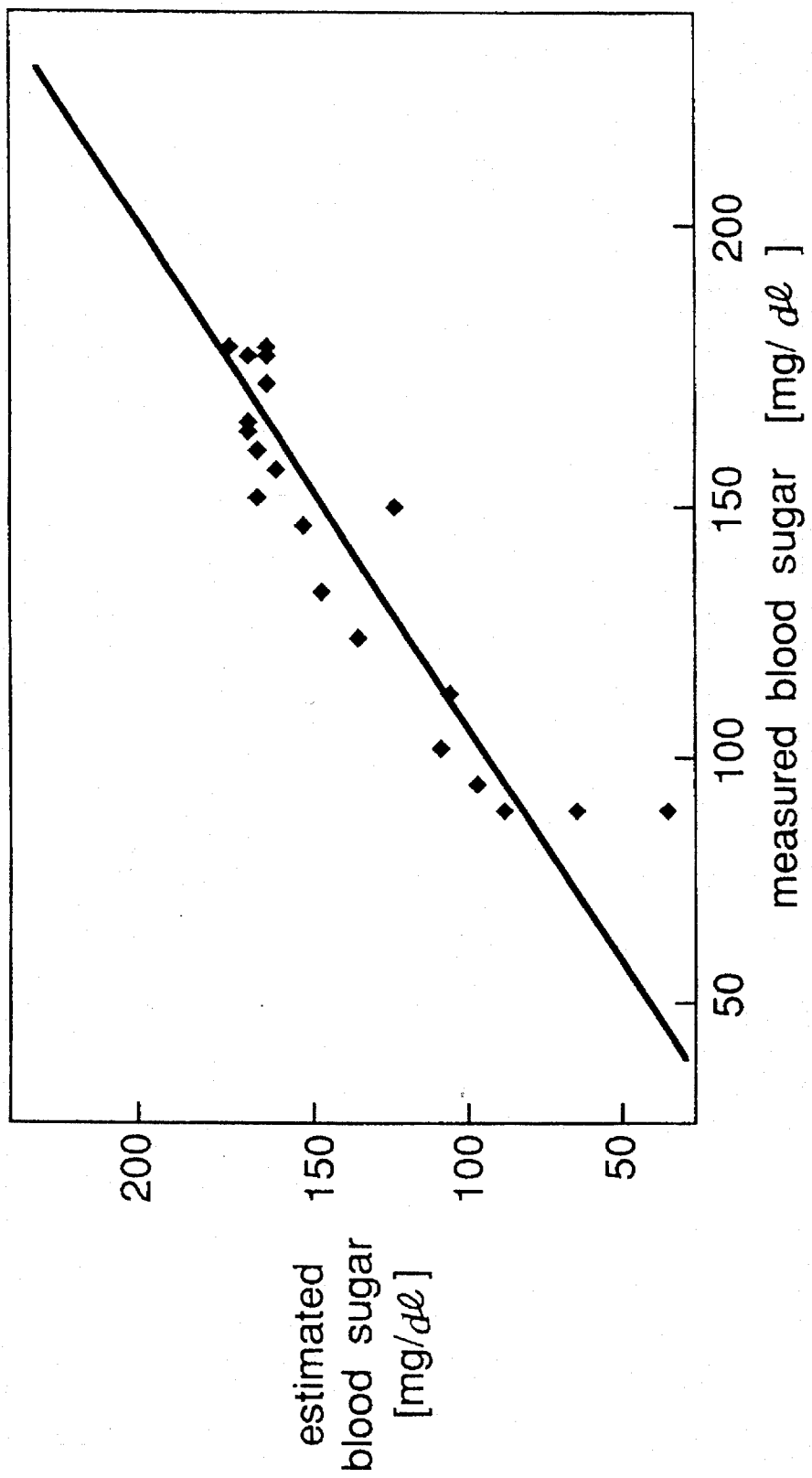
FIG. 14 shows results of quantitative analysis in the case of taking ratios for single wavelength.

(6) The Fourier transform:

The spectra obtained by the Fourier transform from the 11 energy spectra of transmitted light measured every 5 minutes of the commercial milk shown in FIG. 1 are shown in FIG. 11. Their CV spectrum is shown in FIG. 12.

If we compare the CV spectrum of FIG. 6 with the CV spectra of FIG. 2, 4, 10, and 12, then the CV spectral values obtained by ratio calculation in subdomains are smaller, as a whole, than the CV spectral values obtained by no processing, ratio calculation for single wavelength, first-order differentiation, second-order differentiation, and the Fourier transform. Therefore, it is seen that the energy spectra obtained by ratio calculation in subdomains are comparatively stable.

SECOND EMBODIMENT

After an examined subject drank a sugar-loaded aqueous test solution (model name: Trelan 75) manufactured by Shimizu Pharmaceutical Co., we irradiated a finger of the subject with near-infrared light to measure energy spectra of reflected light every 12 minutes using near-infrared spectroscope (model name: System 2000) manufactured by Parkin-Elmer Co. At the same time of the measurement of energy spectra of reflected light, we measured the blood sugar of the subject with a glucose monitor (model name: GM-1320) manufactured by Kyoto Daiichi Kagaku Co., Ltd. We conducted the simultaneous measurement 44 times in total. Then we performed, for the measurements of the reflected energy spectra obtained with the near-infrared spectroscope, (1) no processing, (2) processing of obtaining the ratio of each measured energy value to the measured energy value at a single wavelength, (3) processing of obtaining the ratio of each measured energy value to the measured energy value at a predetermined wavelength within each subdomain, (4) first-order differentiation, (5) second-order differentiation, and (6) the Fourier transform. Here, in the above (2) ratio calculation for single wavelength, we divided each of the following energy values outside the parentheses by the energy value at wavelength 6000 $cm^{-1}$. In the above (3) ratio calculation in subdomains, we divided each of the following measured energy values outside the parentheses by the energy value at the wavelength shown within the parentheses.

4250 $cm^{-1}$ (4300 $cm^{-1}$), 4350 $cm^{-1}$ (4400 $cm^{-1}$),
4450 $cm^{-1}$ (4700 $cm^{-1}$), 4500 $cm^{-1}$ (4700 $cm^{-1}$),
4550 $cm^{-1}$ (4700 $cm^{-1}$), 4600 $cm^{-1}$ (4700 $cm^{-1}$),
4650 $cm^{-1}$ (4700 $cm^{-1}$), 4750 $cm^{-1}$ (4700 $cm^{-1}$),
4800 $cm^{-1}$ (4700 $cm^{-1}$), 4850 $cm^{-1}$ (4700 $cm^{-1}$),
5500 $cm^{-1}$ (6300 $cm^{-1}$), 5600 $cm^{-1}$ (6300 $cm^{-1}$),
5700 $cm^{-1}$ (6300 $cm^{-1}$), 5800 $cm^{-1}$ (6300 $cm^{-1}$),
5900 $cm^{-1}$ (6300 $cm^{-1}$), 6000 $cm^{-1}$ (6300 $cm^{-1}$),
6100 $cm^{-1}$ (6300 $cm^{-1}$), 6200 $cm^{-1}$ (6300 $cm^{-1}$),
6400 $cm^{-1}$ (6300 $cm^{-1}$), 6500 $cm^{-1}$ (6300 $cm^{-1}$),
6700 $cm^{-1}$ (7100 $cm^{-1}$), 6800 $cm^{-1}$ (7100 $cm^{-1}$),
6900 $cm^{-1}$ (7100 $cm^{-1}$), 7000 $cm^{-1}$ (7100 $cm^{-1}$), 7200 cm$^{-1}$ (7100 cm$^{-1}$), 7300 cm$^{-1}$ (7100 cm$^{-1}$), 7400 cm$^{-1}$ (7100 cm$^{-1}$), 7500 cm$^{-1}$ (7100 cm$^{-1}$).

Of the data obtained by the above simultaneous measurement conducted 44 times, we used the 22 sets of data obtained at even-numbered times for making the analytical curve. We used the 22 sets of data obtained at odd-numbered times for estimating the concentration. In particular, we used the values of absorbance at the 28 wavelengths shown outside the parentheses above, and performed quantitative analysis by processing these values of absorbance based on the PLS multivariate analysis.

The results of the quantitative analysis based on (1) no processing, (2) processing of obtaining the ratio of each measured energy value to the measured energy value at a single wavelength, (3) processing of obtaining the ratio of each measured energy value to the measured energy value at each predetermined wavelength within each subdomain, (4) first-order differentiation, (5) second-order differentiation, and (6) the Fourier transform are respectively shown in FIGS. 13, 14, 15, 16, 17, and 18. The correlation coefficients R and estimate errors SEP for the concentration are shown in the following Table 1.

Here, the estimated error SEP for concentration is defined by the following equation (24).

$$SEP = \sqrt{\frac{\sum_{h=1}^{n}(C_{h,i,ref}-C_{h,i,obs})^2}{n}}, \quad (24)$$

where $C_{h,i,ref}$: actual measurement of concentration of component i at hth measurement, $C_{h,i,obs}$: estimated concentration of component i at hth measurement, n: data size for estimation of concentration.

TABLE 1

Results of Divided Quantitative Analysis

| | Least square regression equation | Correlation coefficient R | Estimate error SEP [mg/dl] for concentration |
|---|---|---|---|
| No processing | y = −13.5231 + 1.08041x | 0.923082 | 14.5359 |
| Single-wavelength normalize | y = −10.6919 + 1.05423x | 0.919328 | 14.6042 |
| Subdomain normalize | y = −19.4918 + 1.11672x | 0.947856 | 12.7113 |
| First-order differentiation | y = 35.7489 + 0.657103x | 0.669839 | 28.3899 |
| Second-order differentiation | y = 20.5183 + 0.998778x | 0.882189 | 26.3624 |
| Fourier transform | y = −12.8506 + 1.07155x | 0.93135 | 13.6366 |

Figure 15:
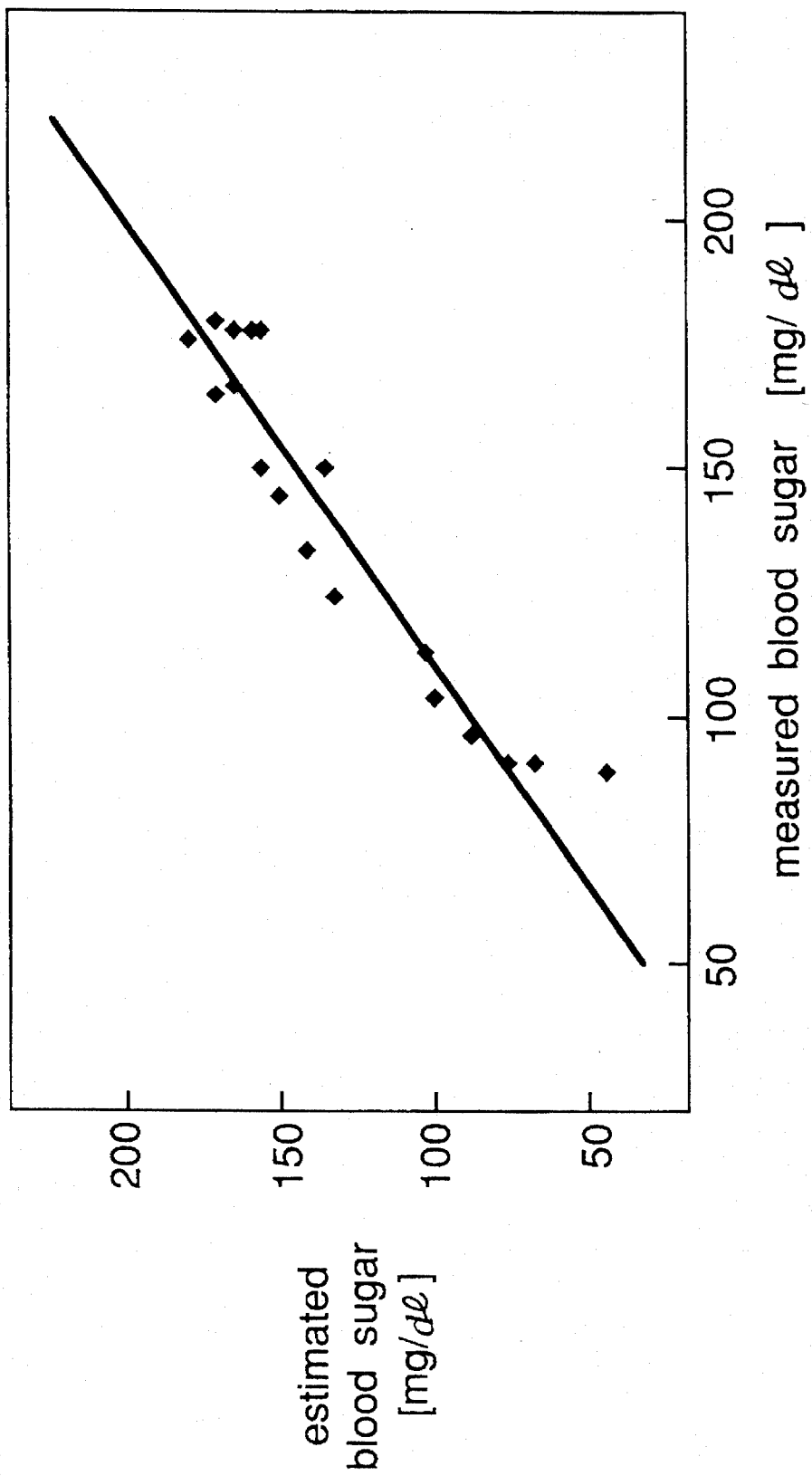
FIG. 15 shows results of quantitative analysis in the case of taking ratios in subdomains.
Figure 16:
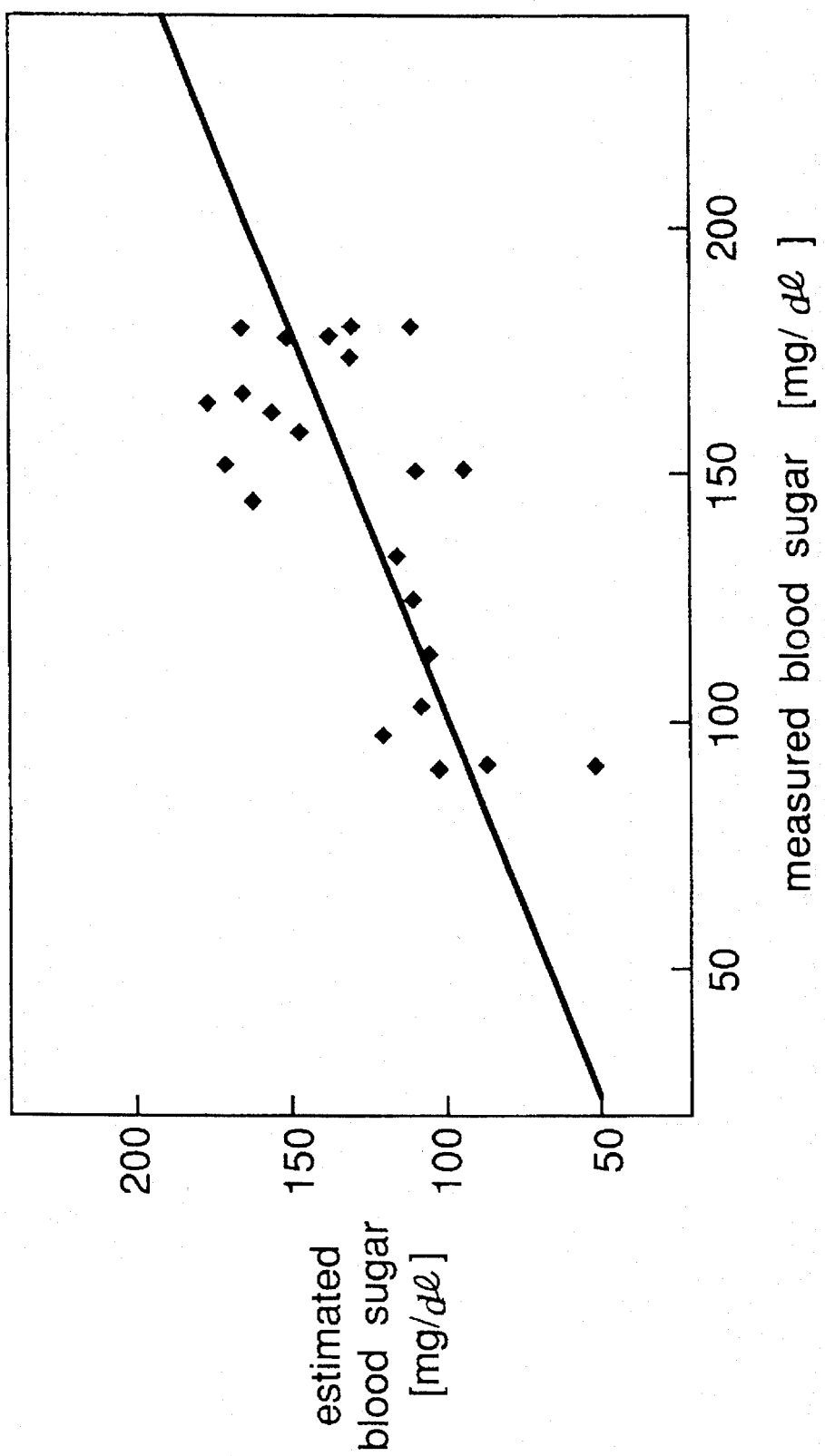
FIG. 16 shows results of quantitative analysis in the case of first-order differentiation.
Figure 17:
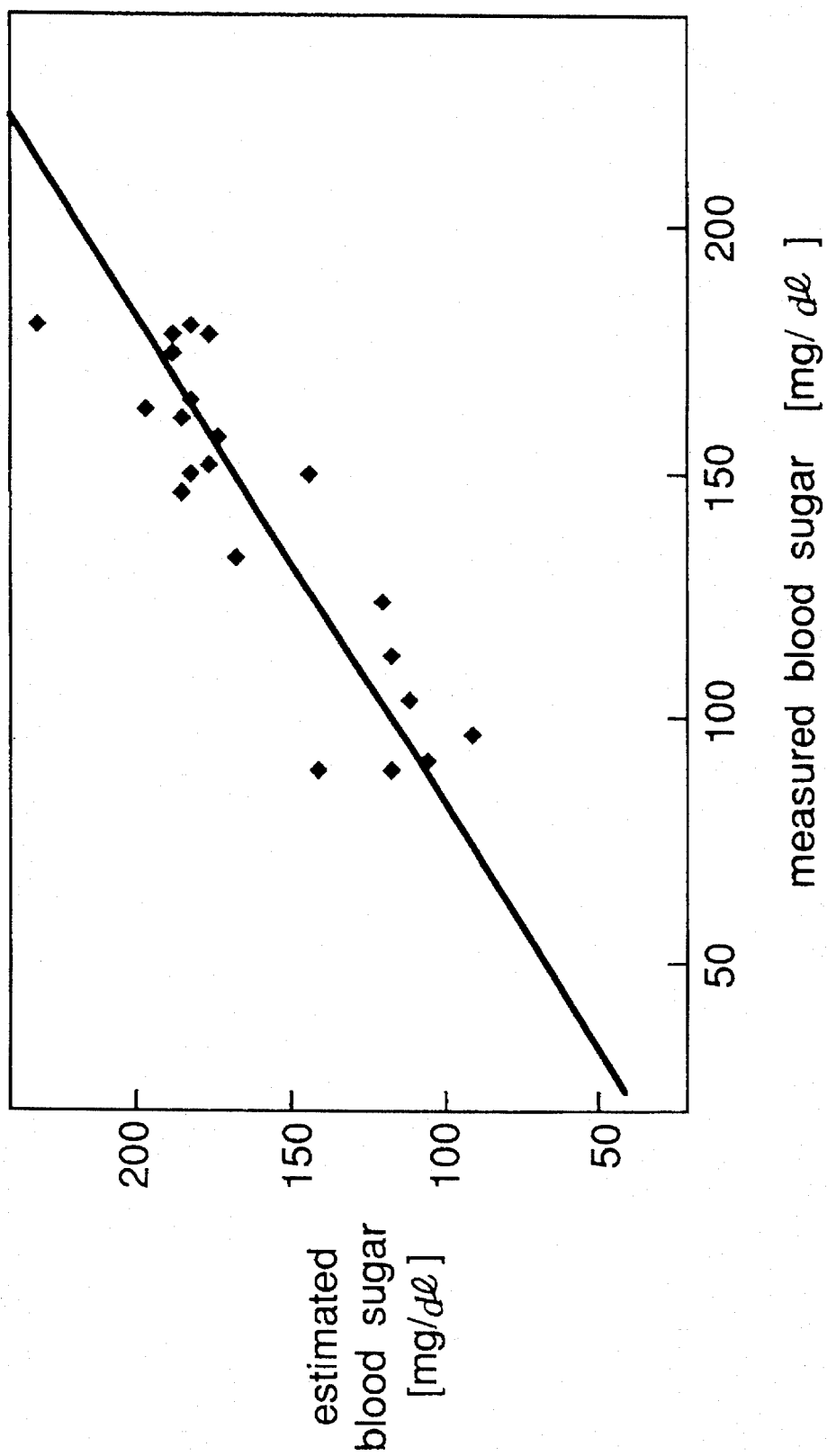
FIG. 17 shows results of quantitative analysis in the case of second-order differentiation.
Figure 18:
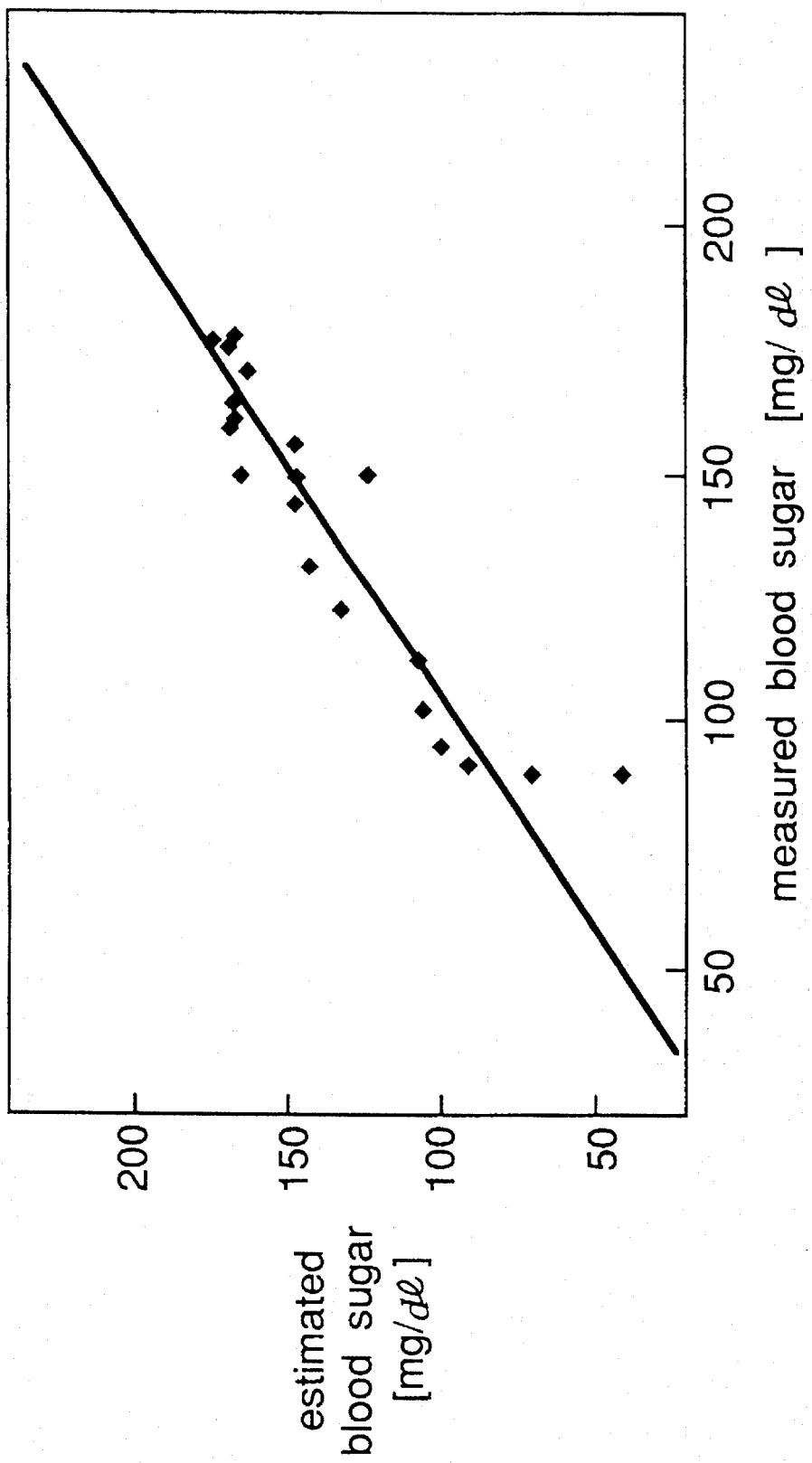
FIG. 18 shows results of quantitative analysis in the case of performing the low-frequency filtering Fourier transform.

If we compare FIG. 15 with FIGS. 13, 14, 16, 17, and 18, then we see that we can obtain blood sugar estimates closer to actual measurements of blood sugar by taking the ratios of energy spectra in subdomains, so that quantitative analysis of concentration has been improved. Further, from Table 1, we see that the correlation coefficient of between blood sugar estimated and observed is greater by taking the ratios of energy spectra in subdomains than each correlation coefficient of blood sugar estimates by (1) no processing, (2) ratio calculation for single wavelength, (4) first-order differentiation, (5) second-order differentiation, and (6) the Fourier transform. Further, the estimates error for concentration SEP is minimum for ratio calculation in subdomains.

THIRD EMBODIMENT

We investigated the fluctuations of the surface transmittance $p(\lambda, \theta_i)$ due to changes of the incidence angle $\theta_i$, when light is made incident from air on water, and compared the case in which ratio calculation was performed with the case in which ratio calculation was not performed.

We obtained the relative change amount $\Delta p(\lambda, \theta_i)/p(\lambda,\theta_i)$ in surface transmittance $p(\lambda, \theta_i)$ due to the change amount $\Delta\theta_i=\theta_{i,1}-\theta_{i,2}$ of the incidence angle $\theta_i$, when ratios were not taken, by the following equation (25).

$$\Delta p(\lambda,\theta_i)/p(\lambda,\theta_i)=\{p(\lambda,\theta_{i,1})_{\|}-p(\lambda,\theta_{i,2})_{\|}\}/p(\lambda,\theta_{i,1})_{\|}. \quad (25)$$

On the other hand, we obtained the relative change amount $\Delta p_N(\lambda, \theta_i)/p_N(\lambda, \theta_i)$ in surface transmittance $p_N(\lambda, \theta_i)$ due to the change amount $\Delta\theta_i=\theta_{i,1}-\theta_{i,2}$ of the incidence angle $\theta_i$, when ratios were taken, by the following equation (26).

$$\Delta p_N(\lambda,\theta_i)/p_N(\lambda,\theta_i)=\{p(\lambda,\theta_{i,1})_{\|}/p(\lambda_r,\theta_{i,1})_{\|}-p(\lambda,\theta_{i,2})_{\|}/p(\lambda_r,\theta_{i,2})_{\|}\}/\{p(\lambda,\theta_{i,1})_{\|}/p(\lambda_r,\theta_{i,1})_{\|}\}. \quad (26)$$

The calculated results are shown in the following Tables 2 and 3.

TABLE 2

| Wavelength (μm) | $n_1$ | $n_2$ | $\theta_i$ (rad) | $p(\lambda, \theta)_{\|}$ |
|---|---|---|---|---|
| 1.256 | 1.00027 | 1.3210 | 0 | 0.980910 |
| 1.256 | 1.00027 | 1.3210 | 5 | 0.981035 |
| 1.256 | 1.00027 | 1.3210 | 10 | 0.981416 |
| 1.256 | 1.00027 | 1.3210 | 15 | 0.982063 |
| 1.256 | 1.00027 | 1.3210 | 20 | 0.982997 |
| 1.256 | 1.00027 | 1.3210 | 25 | 0.984242 |
| 0.6563 | 1.00028 | 1.3311 | 0 | 0.979864 |
| 0.6563 | 1.00028 | 1.3311 | 5 | 0.979996 |
| 0.6563 | 1.00028 | 1.3311 | 10 | 0.980396 |
| 0.6563 | 1.00028 | 1.3311 | 15 | 0.981076 |
| 0.6563 | 1.00028 | 1.3311 | 20 | 0.982056 |
| 0.6563 | 1.00028 | 1.3311 | 25 | 0.983363 |

Here, $n_1$: index of refraction of air, cited from Rika Nenpyo, National Astronomical Observatory (Maruzen Co.), $n_2$: index of refraction of water, calculated from the foiling equation (27) described in Rika Nenpyo.

$$(n_2-1)\times 10^8=6432.8+2949810/(146-1/\lambda^2)+25540/(41-1/\lambda^2). \quad (27)$$

TABLE 3

| $\theta_{i,1}$ (rad) | $\theta_{i,2}$ (rad) | $\Delta p(\lambda, \theta_i)/p(\lambda, \theta_i)$ (rad$^{-1}$) | $\Delta p_N(\lambda, \theta_i)/p_N(\lambda, \theta_i)$ (rad$^{-1}$) |
|---|---|---|---|
| 0 | 5 | 1.2743 × 10$^{-4}$ | 7.2789 × 10$^{-6}$ |
| 0 | 10 | 5.1584 × 10$^{-4}$ | 2.7070 × 10$^{-5}$ |
| 10 | 15 | 6.5925 × 10$^{-4}$ | 3.4321 × 10$^{-5}$ |
| 20 | 25 | 1.2665 × 10$^{-3}$ | 6.2460 × 10$^{-5}$ |

As seen from the above Table 3, the relative change amount $\Delta p_N(\lambda, \theta_i)/p_N(\lambda,\theta_i)$ in surface transmittance $p_N(\lambda, \theta_i)$ is smaller than the relative change amount $\Delta p(\lambda, \theta_i)/p(\lambda,\theta_i)$ in surface transmittance $p(\lambda, \theta_i)$. Therefore, changes in the surface transmittance $p(\lambda, \theta)$ due to changes of the incidence angle $\theta_i$ are reduced by performing ratio calculation. That is, the fluctuations of transmittance due to changes of the incidence angle of light with the measured object can be reduced.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

What is claimed is:

1. A method of stabilizing spectra in spectrometry that performs quantitative analysis of a specific component in an object to be measured by irradiating light to said object and by measuring one of the spectra selected from the energy spectrum of transmitted light, the energy spectrum of scattered light and the energy spectrum of reflected light, comprising steps of measuring an energy spectrum of light transmitted through or reflected from said object;

dividing said energy spectrum into a plurality of wavelength domains, thereby obtaining a plurality of partial energy spectra;

normalizing each of said plurality of partial energy spectra within each wavelength domain using an energy measured at a predetermined wavelength contained in said each wavelength domain; and performing said quantative analysis of a specified component in said object using said plurality of partial energy spectra having been normalized.

2. The method of stabilizing spectra in spectrometry according to claim 1 wherein said quantative analysis of a specific component is performed by multivariate analysis for said plurality of partial energy spectra having been normalized.

3. The method of stabilizing spectra in spectrometry according to claim 1 or 2 wherein said predetermined wavelength is a center value of each wavelength domain.

4. The method of stabilizing spectra in spectrometry according to claim 1 or 2 wherein said specific component is glucose.

* * * * *